United States Patent [19]

Gonzenbach

[11] Patent Number: 4,908,349
[45] Date of Patent: Mar. 13, 1990

[54] BICYCLIC ALDEHYDES AND FRAGRANCE COMPOSITIONS CONTAINING SAME

[75] Inventor: Hans-Ulrich Gonzenbach, Geneva, Switzerland

[73] Assignee: Givaudan Corporation, Clifton, N.J.

[21] Appl. No.: 219,018

[22] Filed: Jul. 14, 1988

[30] Foreign Application Priority Data

Jul. 29, 1987 [CH] Switzerland .......................... 2892/87

[51] Int. Cl.$^4$ .......................... A61K 7/46; C07C 47/52
[52] U.S. Cl. .......................... 512/26; 512/17; 568/425; 568/448
[58] Field of Search .................... 512/17, 26; 568/425, 568/448

[56] References Cited

U.S. PATENT DOCUMENTS 2,800,511  7/1957  Carpenter et al. .................... 512/17
3,278,622  10/1966  Stofberg et al. .

FOREIGN PATENT DOCUMENTS 1468755  5/1969  Fed. Rep. of Germany ........ 512/26
1146023  11/1957  France ................................. 512/26

OTHER PUBLICATIONS

L. Fieser et al., "Reagents for Organic Synthesis", John Wiley and Sons, Inc., 1968, p. 220.
A. Rieche et al., Ber. 92, (1959) 83–91.
H. Gross et al., Ber. 96, (1963) 308–13.
T. Wood et al., J. Org. Chem. 28, (1963) 2248–55.
T. Wood "Givaudanian", Sep., 1968, 5–9.
"Fragrance Chemistry, The Science of the Sense of Smell" E. Theimer, Ed., Ac. Press (1982) 519–34.
"Organikum, Organisch—Chemisches Grundpraktikum" 6th Edition, VEB Deutscher Verlag der Wissenschaften, Berlin, 1967, 335–39.

Primary Examiner—Werren B. Lone
Attorney, Agent, or Firm—Robert F. Tavares; Linda A. Vag

[57] ABSTRACT

Novel odorants of the formula

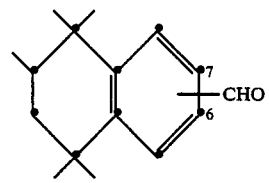

namely, 1,1,2,4,4-pentamethyl-6-formyl-1,2,3,4-tetrahydronaphthalene (1a) and 1,1,2,4,4-pentamethyl-7-formyl-1,2,3,4-tetrahydronaphthalene (1b), possess powerful, very natural-warm, musk-like odor notes.

6 Claims, No Drawings

BICYCLIC ALDEHYDES AND FRAGRANCE COMPOSITIONS CONTAINING SAME

SUMMARY OF THE INVENTION

The present invention concerns the novel bicyclic aldehydes 1,1,2,4,4-pentamethyl-6-formyl-1,2,3,4-tetrahydronaphthalene (1a) and 1,1,2,4,4,-pentamethyl-7-formyl-1,2,3,4-tetrahydronaphthalene (1b) which can be represented by the formula

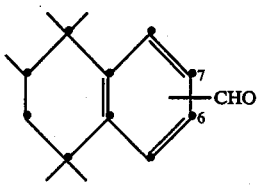

I wherein the numbers, 6 and 7, designated the two carbons which may contain the formyl substituent —CHO.

The bicyclic aldehydes of formula I posses powerful and very natural-warm, musk-like odors with dry, woody, patchouli-like notes. These olifactive properties make the aldehydes particularly valuable for use in fragrance compositions. The invention, therefore, also concerns fragrance compositions containing the aldehydes of formula I and methods for making same.

DESCRIPTION OF THE PREFERRED EMBODIMENTS

The novel bicyclic aldehydes of formula I may be prepared by adapting methods known to the useful for the preparation of aromatic aldehydes such as oxidizing an aromatic methyl group or introducing a formyl group directly into an aromatic ring. For example, aldehyde 1b can be prepared by the oxidation of the aromatic methyl group of the hexamethyltetralin of formula II.

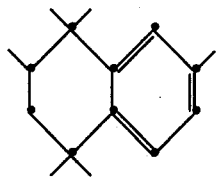

II (See for example, Organikum, Organisch-chemisches Grundpraktikum, 6th Edition VEB Deutscher Verlag der Wissenschaften, Berlin 1967; p. 335 seq.). Suitable oxidizing agents would be oxides such as $CrO_3$, $SeO_2$ and $MnO_2$. It is especially preferred to use $MnO_2$ in $H_2SO_4$ or Mn(III) salts. The oxidation may be carried out at a temperature range of about 50° C. to about 100° C. in an inert solvent such as cyclohexane, ethanol, xylene, naphthalene, dioxan and the like. Example 1 illustrates a suitable oxidation method.

The aldehydes of formula I may also be prepared by introducing a formyl group into the aromatic ring of the pentamethyltetralin of formula III.

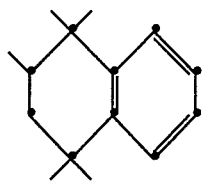

III

A suitable formylation method is that taught by A. Rieche et al. which utilizes 1,1-dichlorodimethyl ether as the formylating agent. (See L. F. Fieser and M. Fieser, Reagents for Organic Synthesis, John Wiley & Sons, Inc., 1967, 220 and references mentioned therein.) This method produces a mixture of aldehydes of formulas 1a and 1b. Example 2 illustrates a method suitable for carrying out this formylation. The aldehydes, which are obtained in a 1:1 mixture, may be separated by crystallization of aldehyde 1b from the mixture or may be used as such. The olfactive properties of aldehydes 1a and 1b are found to be of a similar nature, such that either aldehyde, or a mixture thereof, can be used to achieve similar effects in the formulation of a fragrance composition.

Both aldehydes 1a and 1b are distinguished by powerful and very natural-warm odor notes in the direction of musk with a radiant, dry woody note in the direction of patchouli. The latter note may predominate in compositions whereby there is observed simultaneously, pronounced harmonizing effects which, usually, can only be achieved with the use of ethereal oils. Such compositions are distinguished by a strong diffusion and a greatly improved substantivity.

Known aldehydes having structures related to aldehydes 1a and 1b do not have the desirable olfactive properties possessed by the aldehydes of this invention. For example, aldehyde IV is described as having a weak amber note ("The Givaudanian" September (1968).

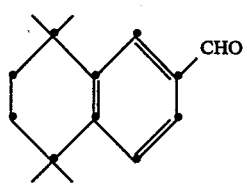

IV (See also J. Org. Chem. 28, 2248, 1963.) Aldehyde V

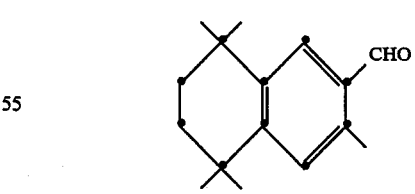

V is described as having a musk note (U.S. Pat. No. 2,800,511) but on comparison of a 5% alcoholic solution of aldehyde V with a similar solution of aldehyde I, aldehyde V is found by perfumers to be powdery, less intense and as having a metallic top note.

On the basis of their natural olfactory notes the aldehydes of formula I are especially suitable for the modification of known compositions. Of particular note is the manner in which they are found to round-off and harmonize the olfactory notes of known compositions without dominating in an unpleasant manner.

The aldehydes of formula I combine with numerous known odorant ingredients of natural or synthetic origin, whereby the range of the natural raw materials can embrace not only readily-volatile, but also moderately-volatile and difficulty-volatile components, and that of the synthetics can embrace representatives from practically all classes of substances, as is evident from the following compilation:

Natural products, such as tree moss absolute, basil oil, citrus oils (such as bergamot oil, mandarin oil, etc.), mastix absolute, myrtle oil, palmarosa oil, patchouli oil, petitgrain oil, Paraquay, wormwood oil, alcohols, such as farnesol, geraniol, linalool, nerol, phenylethyl alcohol, rhodinol, cinnamic alcohol, aldehydes, such as citral, α-hexylcinnamaldehyde, hydroxycitronellal, Lilial ® (Givaudan) (p-tert-butyl-α-methyldihydrocinnamaldehyde), methyl-nonylacetaldehyde, α-methyl-3,4-methylenedioxyhydrocinnamic aldehyde, ketones, such as allylionone, α-ionone, β-ionone, isoraldeine ® (Givaudan) (isomethyl-α-ionone), methylionone, esters, such as allyl phenoxyacetate, benzyl salicylate, cinnamyl propionate, citronellyl acetate, citronellyl ethoxolate (citronellyl.O—CO—OC.OC$_2$H$_5$), decyl acetate, dimethylbenzylcarbinyl acetate, dimethylbenzylcarbinyl butyrate, ethyl acetoacetate, hexenyl isobutyrate, linalyl acetate, methyl dihydrojasmonate, styrallyl acetate, vetiveryl acetate, etc.

lactones, such as γ-undecalactone, various components often used in perfumery, such as musk ketone, indole, p-methane-8-thiol-3-one, methyleugenol.

The aldehydes of formula I (or mixtures thereof) can be used in wide ranges which can extend, for example, from about 0.1% (detergents) to about 20% (alcoholic solutions). It will be appreciated that these values are not limiting values, as the experienced perfumer can also achieve effects with still lower concentrations or can synthesize novel complexes with even higher amounts. The preferred concentrations range between about 1% and about 10%. The compositions manufactured with the formula I aldehydes can be used for all kinds of perfumed consumer goods (eau de cologne, eau de toilette, extracts, lotions, creams, shampoos, soaps, salves, powders, toothpastes, mouth washes, deodorants, detergents, fabric conditioners, tobacco, etc.).

The aldehydes of formula I can accordingly be used in the manufacture of compositions and, as will be evident from the above compilation, a wide range of known odorants or odorant mixtures can be used. In the manufacture of such compositions the known odorants mentioned above can be used according to methods known to the perfumer, such as e.g. from W. A. Poucher, Perfumes, Cosmetics and Soaps 2, 7th edition, Chapman and Hall, London, 1974.

ILLUSTRATIONS OF THE PREFERRED EMBODIMENTS

Example 1

To a 4-necked flask equipped with a mechanical stirrer, dropping funnel, reflux condenser and thermometer there is added 580 g of 70% sulphuric acid. While stirring at 60° C. there is now rapidly added dropwise a solution of 308 g of 1,1,2,4,4,7-hexamethyl-1,2,3,4-tetrahydronaphthalene in 500 ml of cyclohexane.

At this temperature 209 g of manganese dioxide are added in small portions within a quarter of an hour. The temperature rises to 65° and is increased to 80° C., at which temperature the mixture is stirred for 4 hours. Thereafter, the mixture is filtered while hot (Buchner funnel having 20 g of Celatom FW 50 as a filter aid) and rinsed with 400 ml of hot cyclohexane. The combined filtrates are washed neutral with water and NaHCO$_3$ solution and concentrated on a rotary evaporator. There are obtained 308 g of crude product consisting of a 2:1 mixture of starting material and desired aldehyde 1b (GC, Carbowax 20 M/220° C.). Distillation over a Goodloe 0column yields the pure aldehyde 1b in 23% yield, boiling point 118° C./0.5 mmHg, purity (GC)>95%. Recrystallization from ethanol yields 99% material having a melting point of 77.5°–78.5° C.

Example 2

The hydrocarbon 1,1,2,4,4-pentamethyl-1,2,3,4-tetrahydronaphthalene is placed in methylene chloride and treated at −20° C. with an equimolar amount of TiCl$_4$. While stirring there is added dropwise, likewise in an equimolar amount, 1,1,-dichlorodimethyl ether and the temperature is brought to +30° C. within the following 4.5 hours. The mixture is subsequently poured onto ice, extracted with ether and washed neutral with saturated NaCl, dilute NaHCO$_3$ and saturated NaCl, dried over MgSO$_4$ and evaporated and distilled in a vacuum. The crude product obtained is recrystallized from ethanol and now exhibits an only insignificantly broader melting point interval than in the case of Example 1. By gas chromatography (capillary column SE 30) it cannot be differentiated form 1b. In accordance with NMR data (400 Mhz) it is a 1:1 mixture of the aldehydes 1a and 1b.

By repeated crystallization from alcohol there is obtained an enriched fraction of 1b (purity 90%) which is identical with the material from Example 1 (GC and MNR). The other isomer (1a), the identity of which can be established by NMR comparison with 1b, remains in the mother liquors, purity>90% (NMR). Olfactorily 1a and 1b are very similar, that is to say in practice they can hardly be differentiated and therefore in use they can be exchanged with each other or can be used as a mixture.

Example 3

(a) Compositions having a floral, fresh, powdery hesperidine note

| | Parts by weight |
|---|---|
| Ethyl vanillin | 1 |
| 2-Methoxy-napthalene | 2 |
| Galbanum essence | 2 |
| Vernaldehyde ® (Givaudan) (1-methyl-4-(4-methyl-pentyl)-3-cyclohexenecarbaldehyde) | 5 |
| Bornyl acetate | 5 |
| Cananga essence | 10 |
| Sandalore ® (Givaudan) (5-(2,3,3-trimethyl-cyclopent-3-enyl)3-methyl-pentan-2-ol) | 15 |
| Petitgrain ess. Paraguay | 20 |
| Verdyl acetate ® (Givaudan) (dihydro-nor-dicyclopentadienyl acetate) | 20 |
| Dimetol ® (Givaudan) (2,6-dimethyl-heptan-2-ol) | 20 |
| Clove leaf oil | 20 |
| Benzyl acetate | 30 |

-continued

| | Parts by weight |
|---|---|
| Coumarin | 30 |
| Terpineol | 30 |
| Methyl cedryl ketone | 40 |
| 1-Methyl-1-methoxy-cyclodedecane | 50 |
| Citronellol | 50 |
| Geraniol | 50 |
| Isoraldeine ® 70 (Givaudan) (isomethyl ionone/ iso-α-4-(2,6,6-trimethyl-2-cyclohexen-1-yl)-3-methyl-3-buten-2-one) | 100 |
| Benzyl salicylate | 100 |
| Tetrahydrolinalool | 100 |
| p-tert-Butylcyclohexyl acetate | 150 |
| Lilial ® (Givaudan) (α-methyl-3-(p-tert-butylphenyl)-propionalhedyde) | 50 |
| | 900 |

The addition of 100 parts by weight of 1b results in the appearance of remarkable intensity, radiance and diffusion.

(b) Tobacco-leather base

| | Parts by weight |
|---|---|
| Celery essence | 1 |
| Helichrysium-(immortelle) resinoid | 1 |
| Cade oil in DPG | 1 |
| 6-sec-Butylquinoline | 1 |
| Cinnamaldehyde | 1 |
| 8α-12-Oxido-12,14,15,16-tetranorlabdane | 1 |
| Eugenol | 1 |
| Ethyl vanillin | 5 |
| Flouve absolute | 5 |
| Phenylpropyl alcohol | 20 |
| Coumarin | 30 |
| Sandalore ® (Givaudan) (5-(2,2,3-trimethyl-cyclopent-3-enyl)-3-methylpentan-2-ol) | 30 |
| Cedarwood essence | 50 |
| Frankincense Resinoid | 50 |
| β-Ionone | 50 |
| Linalool | 50 |
| Linalyl acetate | 100 |
| Amyl salicylate | 100 |
| Patchouli essence | 100 |
| Nonanyl acetate | 100 |
| Isoraldeine ® 70 (Givaudan) (isomethyl-ionone/ iso-α-4-(2,6,6-trimethyl-2-cyclohexen-1-yl)-3-buten-2-one) | 200 |
| Gardenol ™ (Givaudan) (methylphenylcarbinyl acetate) | 3 |
| | 900 |

The addition of 100 parts of aldehyde 1b results in the appearance of a pronounced tobacco note which is decidedly rich, natural and harmonically balanced.

(c) Eau de toilette having the notes: citrus, floral, woody, fresh,

| | Parts by Weight |
|---|---|
| C$_{10}$-Aldehyde | 2 |
| C$_{11}$-Aldehyde | 2 |
| Vanillin | 2 |
| Peche pure (γ-undecalactone) | 2 |
| Ciste labdanum resinoid | 4 |
| Neroli ess. bitter orange | 4 |
| Gardenol ™ (Givaudan) (methylphenylcarbinyl acetate) | 6 |
| Isobutyl-quinoline 10% in DPG | 6 |
| Galbanum essence | 6 |
| Coumarin | 10 |
| Ylang-ylang essence | 10 |

-continued

| | Parts by Weight |
|---|---|
| Lilial ® (Givaudan) (α-methyl-β-(p-tert-butyl-phenyl)propionaldehyde) | 20 |
| Lemarome ® N (Givaudan) (3,7-dimethyl-2,6-octadienal/ citral synthetic | 20 |
| Geranium essence Bourbon | 20 |
| Bois de Santal essence | 20 |
| Dipropylene glycol | 36 |
| Citronellol extra | 40 |
| Vetivenyl acetate Haiti | 40 |
| Mousse de chene abs. 50% in benzyl benzoate | 40 |
| Lavandin essence | 40 |
| Patchouli essence | 60 |
| 1-Methyl-1-methoxy-cylododecane | 60 |
| Isoraldeine ® (Givaudan) (4-(2,6,6-trimethyl-2-cyclohexen-1-yl)-3-methyl-3-buten-2-one/methyl-ionone) | 100 |
| Hydroxycitronellal | 100 |
| α-hexylcinnamaldehyde | 100 |
| Lemon essence | 100 |
| Bergamot essence | 100 |
| | 950 |

By the addition of 50 parts of the aldehyde 1b there results a composition having a pronounced fresh effect, qualified especially by the strong diffusion of the citrus notes. Likewise, the woody notes come forward pleasantly. The composition becomes fully balanced—also in the bottom.

I claim:

1. A compound of the formula

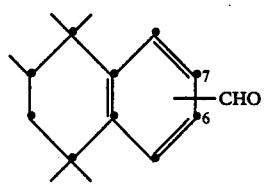

I wherein the group —CHO is a substituent on either the carbon atom designated by the number 6 or on the carbon atom designated by the number 7.

2. The compound according to claim 1 which is 1,1,2,4,4-pentamethyl-6-formyl-1,2,3,4-tetrahydronaphthalene.

3. The compound according to claim 1 which is 1,1,2,4,4-pentamethyl-7-formyl-1,2,3,4-tetrahydronaphthalene.

4. A fragrance composition comprising an olfactorily effective amount of a compound of the formula

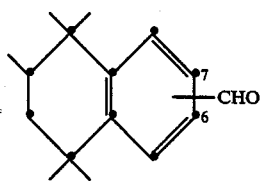

I wherein the group —CHO is a substituent on either the carbon atom designated by the number 6 or on the carbon atom designated by the number 7, and at least one other olfactory agent.

5. The fragrance composition according to claim 4 wherein the compound is 1,1,2,4,4-pentamethyl-6-formyl-1,2,3,4-tetrahydronaphthalene.

6. The fragrance composition according to claim 4 wherein the compound is 1,1,2,4,4-pentamethyl-7-formyl-1,2,3,4-tetrahydronaphthalene.

* * * * *